United States Patent [19]

Sullivan

[11] Patent Number: 4,944,310
[45] Date of Patent: Jul. 31, 1990

[54] DEVICE FOR TREATING SNORING SICKNESS

[75] Inventor: Colin E. Sullivan, Birchgrove, Australia

[73] Assignee: Somed Pty. Ltd., Australia

[21] Appl. No.: 292,646

[22] Filed: Dec. 29, 1988

Related U.S. Application Data

[63] Continuation of Ser. No. 941,542, Dec. 11, 1986, abandoned, which is a continuation of Ser. No. 773,244, Sep. 3, 1985, abandoned, which is a continuation of Ser. No. 456,046, filed as PCT AU82/00063 on Apr. 23, 1982, published as WO82/03548 on Oct. 25, 1982, abandoned.

[30] Foreign Application Priority Data

Apr. 24, 1981 [AU] Australia .............................. PE8570

[51] Int. Cl.$^5$ ............................................. A62B 18/02
[52] U.S. Cl. ............................. 128/848; 128/205.25; 128/207.13; 128/207.18
[58] Field of Search .............. 128/848, 207.12, 207.13, 128/206.11, 207.18, 204.18, 204.21, 205.24, 205.25, 204.75, 203.28, 205.11, 200.25

[56] References Cited

U.S. PATENT DOCUMENTS

| | | | |
|---|---|---|---|
| 1,632,449 | 6/1927 | McKesson | 128/207.13 |
| 3,889,671 | 6/1975 | Baker | 128/207.13 |
| 3,902,486 | 10/1975 | Guichard | 128/206.11 |
| 4,151,843 | 5/1979 | Brekke | 128/205.25 |
| 4,156,426 | 5/1979 | Gold | 128/207.18 |
| 4,249,527 | 2/1981 | Ko et al. | 128/204.18 |
| 4,266,540 | 5/1981 | Panzik et al. | 128/205.25 |

FOREIGN PATENT DOCUMENTS

| | | | |
|---|---|---|---|
| 701690 | 1/1941 | Fed. Rep. of Germany | 128/207.13 |
| 863412 | 4/1941 | France | |
| 27599 | of 1903 | United Kingdom | 128/207.13 |
| 483502 | 4/1938 | United Kingdom | 128/207.12 |

OTHER PUBLICATIONS

The Lancet "Reversal of Obstructive Sleep Apnoe . . . ", Apr. 18, 1981, pp. 862, 863, 865.

Primary Examiner—Max Hindenburg
Assistant Examiner—J. P. Lacyk
Attorney, Agent, or Firm—Ladas & Parry

[57] ABSTRACT

A device which may be used in the treatment of snoring sickness. An air blower supplies high volume air at slightly greater than atmospheric pressure to a flexible tube (2). Such air is communicated via tube (2) through nose piece (3), further through flexible tube (4) and a restrictive air outlet device (9). Communicating with nose piece (3) is a face mask (5) adapted to be sealingly attached to a patient's nose and providing communication between the patient's nostrils and the interior of nose piece (3). By varying the restriction of device (9) the air pressure at the region of nose piece (3) and also the patient's nostrils can be varied.

12 Claims, 3 Drawing Sheets

DEVICE FOR TREATING SNORING SICKNESS

This is a continuation of co-pending application Ser. No. 06/941,542 filed on Dec. 11, 1986, now abandoned which is a continuation of Ser. No. 773,244, filed on Sept. 3, 1985 now abandoned which is a continuation of Ser. No. 456,046 filed as PCT AU82/00063 on Apr. 23, 1982, published as WO82/03548 on Oct. 25, 1982 now abandoned.

The present invention relates to apparatus which may be used, among other things, for the treatment of Obstructive Sleep Apnoea, more commonly called snoring sickness, which is characterized by occlusion of the upper air passage during sleep. It results from a combination of abnormally restricted upper air passages and the normal loss of muscle tone in the region of the tongue, soft palate and posterior oropharyngeal wall. The condition causes the affected patient to asphyxiate for periods typically of 30 to 120 seconds duration, 200 to 300 times per night. It is a recognized cause of "unexpected" death. In less severe cases it often causes excessive daytime somnolence, heart disorder and brain damage. Some lung diseases are commonly found in association with "snoring" sickness.

The syndrome is a common disorder, particularly in middle aged overweight males, although a person affected may have no awareness of the problem.

BACKGROUND ART

Prior art methods for overcoming the problem include the use of neck collars, respiratory stimulants, loss of weight in cases of obesity and tracheostomys which are left open at night. Only the tracheostomy has been effective in overcoming the problem completely. However in cases where immediate life-threatening complications are not present, the decision as to whether this method should be used or not is obviously difficult.

It is therefore an object of the present invention to provide apparatus which will ameliorate the foregoing disadvantages.

DISCLOSURE OF INVENTION

Accordingly, in one broad form, the invention may be said to consist in apparatus comprising: a length of tubing with at least substantial portions thereof being flexible, having an inlet end for introduction of air under pressure and an outlet end; a nose piece including a cavity shaped for the insertion of a patients nose therein and adapted to be releasably sealed to the patients face in an airtight manner; at least one opening in an intermediate portion of said tubing forming air communication between said intermediate portion and said cavity; and means to effect resistance to air flow through said outlet end of said tubing to maintain air pressure in the region of said at least one opening at slightly greater than atmospheric air pressure when air is forced therethrough.

BRIEF DESCRIPTION OF DRAWINGS

By way of example only, one preferred form of the invention will now be described with reference to the accompanying drawings in which.

BEST MODE OF CARRYING OUT THE INVENTION

Figure 1:
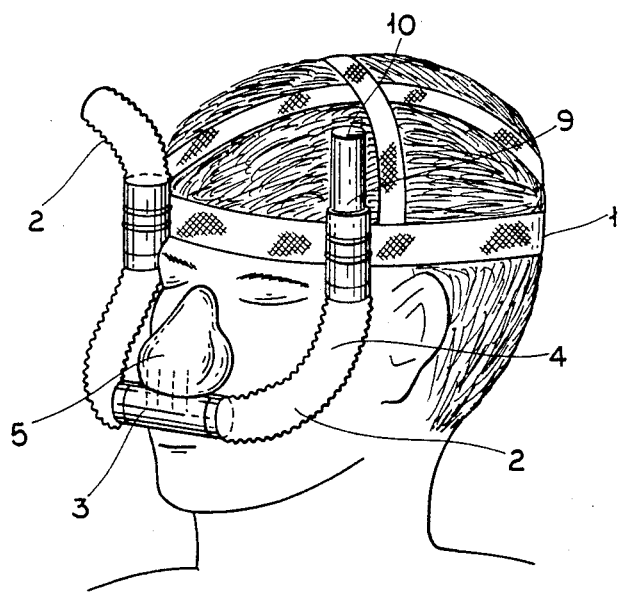
FIG. 1 is a perspective view of a device according to the present invention, absent means for providing air under pressure, in place on a patient.
Figure 2:
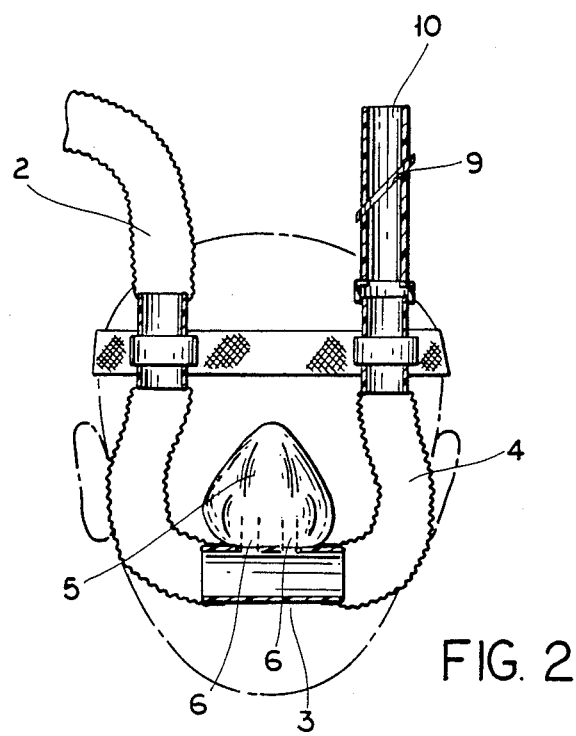
FIG. 2 is a frontal view of the device of FIG. 1.
Figure 3:
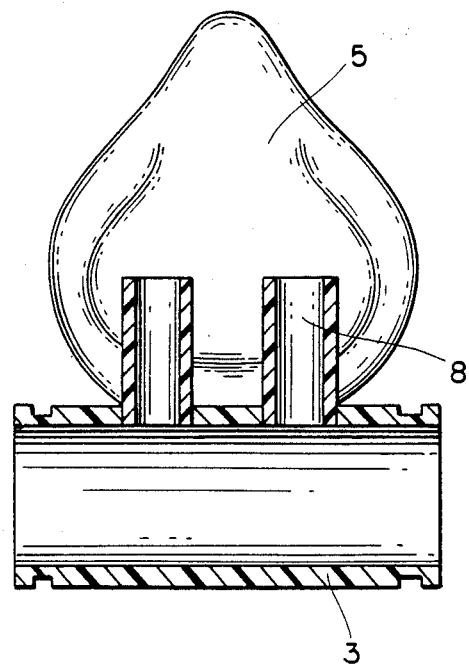
FIG. 3 is a detailed view of a portion of the device of FIG. 1.
Figure 4:
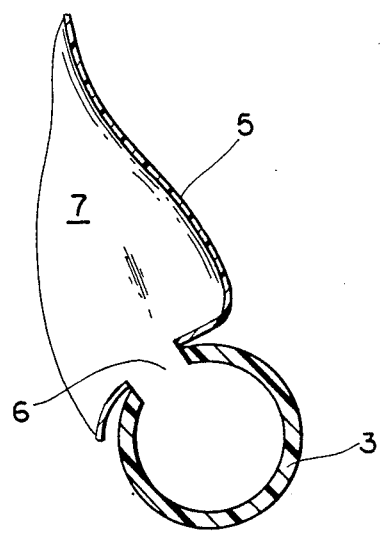
FIG. 4 is a side view of the portion of a device similar to that of FIG. 3 without the nasal tubes.

In FIG. 1 a head band 1, suitably padded, is adapted to fit around the patient's head in a comfortable yet sufficiently firm manner to provide adequate anchorage for the attachment of the components described below. For this purpose commercially available head bands as used with safety hats have been found to be ideal.

A plastic concertina type flexible tube 2 leads from an air blower, or pump means to one side of a rigid tubular nostril piece 3 defining a second chamber. Some small distance from nostril piece 3 flexible tube 2 is fastened to head band 1. Leading out of the opposite side of nostril piece 3 is another length of flexible tubing which forms the expiratory tube 4. Expiratory tube 4 is also fastened to head band 1 so that when the apparatus is placed on the patients head it is held firmly in place although it offers little discomfort to the wearer. Flexible tubes 2 and 4 are adapted so that their ends may pass over the respective open ends of nostril piece 3. The flexible tubes are sealingly secured thereto by light weight electrical type clamping bands. These bands may also be used to so secure flexible tubes 2 and 4 to head band 1.

A mouldable nose mask 5 is attached to, or formed as part of, nostril piece 3. Nose mask 5 is shaped so as to fit over most noses and includes a cavity 7 for this purpose. Communicating between cavity 7 and the interior of nostril piece 3 are two openings 6 which are substantially aligned respectively with a patient's nostrils when nose mask 5 is in place. Optional soft nasal tubes 8 can be inserted into openings 6, or formed as part of nostril piece 3, and are adapted to enter the patient's nostrils in certain difficult cases.

The air supply in the preferred form consists of a high volume air pump similar to a vacuum cleaner running in reverse. For this purpose Hitachi (Registered Trade Mark) vortex blower model VB001S has been found to be ideal. The pump may be placed in a sound deadening box.

A variable restriction device 9 in expiratory tube 4 is incorporated in its end. This restriction allows the air pressure at the nostril piece 3 to be adjusted to suit the particular patient using the apparatus. A typical relative pressure for a patient may be 6 cm $H_2O$ although a range from 4 to 15 cms $H_2O$ would cover most if not all individuals. The exact location of restriction device 9 is not critical although substantial noise reduction is obtained if it is some distance from the final opening 10.

In use a seal is produced from surgical grade silicon, such as Dow Corning Silastic 382 (Registered Trade Mark), rubber by forming it around the inside of cavity 7 and placing the apparatus in its working position on the patient. The seal and apparatus do not extend down over the mouth. This allows breathing through the mouth while the patient is awake even if the apparatus is in place but not supplying air. This is an important safety aspect.

While in operation the apparatus provides a normal air mixture to the nostrils of the patient at an adjustable pressure that is slightly above atmospheric pressure. The pressure is initially set at a low level and while the patient is asleep it is gradually increased until occlusions no longer occur. This set pressure should then be adequate for the patient in the future. Although approx. 4 liters of air per second is delivered by the pump much of this leaves the apparatus, via the end restriction, having never been breathed by the patient. The patient inhales normally, the excess pressure merely overcoming the abnormal resistance of the upper air passages and preventing their inward collapse.

Figure 5:
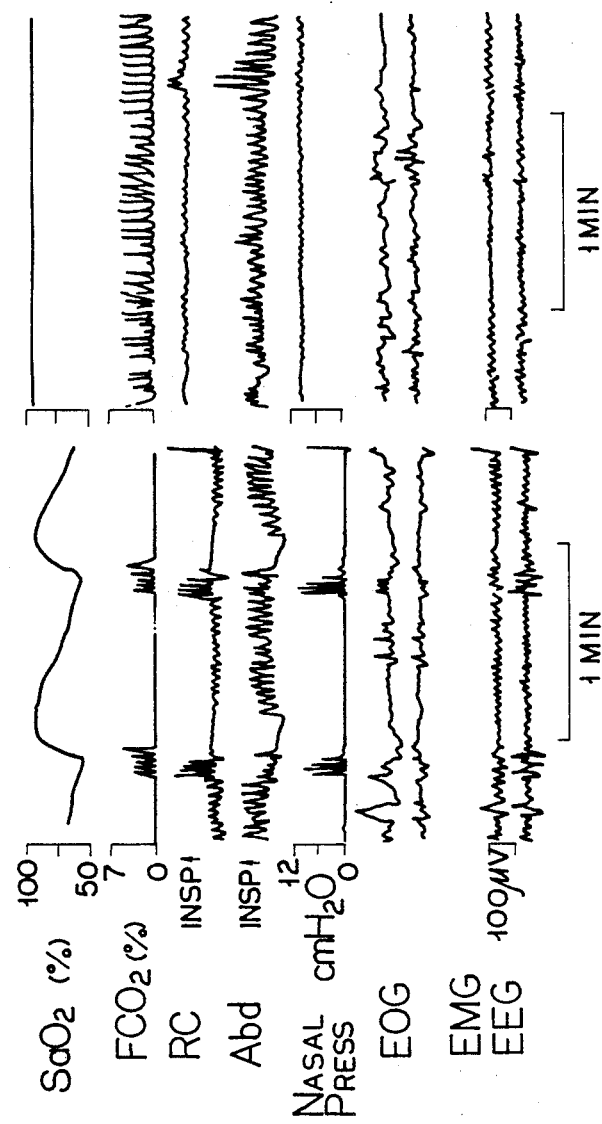
FIG. 5 shows a number of graphs which compare a patients sleep with and without the assistance of the device of FIG. 1.

FIG. 5 shows a part of a polygraph trace taken from a patient with severe sleep apnea, before and during the application of continuous positive airway pressure (CPAP) via a device of the present invention, in rapid-eye-movement sleep. In the left hand panel (without CPAP), periods of total absence of airflow at the nose are apparent in the nasal pressure trace for up to 45 seconds at a time, despite vigorous movements of ribcage and abdominal wall. Arterial haemoglobin oxygen saturation falls with each apnea as low as 55%. Each apnea is terminated by arousal from sleep, indicated by bursts of electromyogram activity and movement artifact on electroencephalogram. A few rapid deep breaths follow. Note low voltage, fast electroencephalogram, minimal electromyogram activity, and abundant rapid-eye-movements between arousals. In the right hand panel 9 cm $H_2O$ CPAP via the nosemask completely prevents obstruction, continuous airflow is evidenced on the pressure tracing, arterial oxygen saturation remains normal, and stable uninterrupted sleep is permitted.

While using the above described device exhaling may be slightly affected by the apparatus, and a raised mean lung volume may result, but at the disclosed pressures no danger would exist or adverse side effects be normally encountered.

The present invention has been described in connection with the treatment of obstructive sleep apnea. Other uses of the apparatus of the invention will be obvious to those skilled in the art and include:
treatment of severe snoring; assistance of breathing during sleep in patients with lung disease;
in intensive care, post-operative and anaesthetic wards to provide continuous positive airway pressure; and
with a conventional respirator to provide assisted positive pressure ventilation in patients with central sleep apnoea (patients who stop breathing during sleep), or sleep hypo-ventilation (patients who don't breath enough during sleep).

The above described apparatus is merely one example of an embodiment of the present invention. Various modifications can be made without departing from the scope of the present invention. For example flexible tubes 2 and 4, nostril piece 3 and nose mask 5 might be moulded in one piece from plastics material.

I claim:

1. Apparatus for maintaining continuous positive airway pressure, said apparatus comprising a nose piece shaped to fit over the nose of a user and defining a first chamber; a large bore inlet tube entering into a second chamber attached to said nose piece and in fluid communication with said first chamber only via at least one orifice interconnecting said chambers, said second chamber having a large bore exit to the atmosphere including continually open resistance means to provide a resistance to the flow of gases through said exit and being located adjacent to said exit; and means to releasably seal said nose piece against the facial skin of said user adjacent to said nose to effect a pressure tight seal of said first chamber; said inlet tube connected to a high volume supply of air to cause a high volume of air to flow through said inlet tube, into said second chamber and out said resistance means, said resistance means causing the pressure within said second chamber to be elevated above, and maintained above, atmospheric pressure, said at least one orifice transmitting said elevated pressure to said first chamber, and the flow of air passing between said second chamber and said first chamber through said orifice being substantially equal to the air inhaled and exhaled by said user via the nose.

2. Apparatus as claimed in claim 1 wherein said resistance means is located at a location spaced from said second chamber.

3. Apparatus as claimed in claim 1 wherein said exit opens into a length of large bore tube separate from said inlet tube.

4. Apparatus as claimed in claim 1 wherein said resistance means comprises an aperture of reduced size relative to said large bore exit.

5. Apparatus as claimed in claim 1 wherein said resistance means is variable and said inlet, second chamber and exit are dimensioned to receive a high volume flow of approximately 4 liters per second.

6. Apparatus as claimed in claim 1 wherein said resistance means is dimensioned to raise the pressure within said first and second chambers to a pressure above atmospheric pressure within the range of from 4 centimeters to 15 centimeters water gauge.

7. Apparatus as claimed in claim 1 wherein said at least one orifice is located in said first chamber at a location opposite the nostrils of said nose.

8. Apparatus as claimed in claim 7 wherein said at least one orifice comprises a pair of orifices.

9. Apparatus as claimed in claim 1 wherein said second chamber is substantially cylindrical having an internal diameter substantially equal to the bore of said inlet tube.

10. Apparatus as claimed in claim 1 wherein said inlet tube and exit are located at opposite sides of said second chamber.

11. Apparatus as claimed in claim 1 wherein a pump means is connected to the large bore inlet tube and supplies a high volume of air.

12. Apparatus for maintaining continuous positive airway pressure, said apparatus comprising a nose piece shaped to fit over the nose of a user and defining a first chamber; a large bore inlet tube entering into a second chamber attached to said nose piece and in fluid communication with said first chamber only via at least one orifice interconnecting said chambers, said second chamber having a large bore exit to the atmosphere including continually over resistance means to provide a resistance to the flow of gases through said exit and being located adjacent to said exit; and means to releasably seal said nose piece against the facial skin of said user adjacent to said nose to effect a pressure tight seal of said first chamber; a pump connected to said inlet tube to supply a high volume of air flow through said inlet tube, into said second chamber, and out of said second chamber and to atmosphere by way of said resistance means, said resistance means causing the pressure within said second chamber to be elevated above, and maintained above, atmospheric pressure, said at least one orifice transmitting said elevated pressure to said first chamber, and the flow of air passing between said second chamber and said first chamber through said orifice being substantially equal to the air inhaled and exhaled by said user via the nose.

* * * * *